(12) United States Patent
Yatsenko et al.

(10) Patent No.: US 7,272,208 B2
(45) Date of Patent: Sep. 18, 2007

(54) SYSTEM AND METHOD FOR AN ADAPTIVE MORPHOLOGY X-RAY BEAM IN AN X-RAY SYSTEM

(75) Inventors: Dimitri Victorovich Yatsenko, Salt Lake City, UT (US); Richard Larry Anderton, West Jordan, UT (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 307 days.

(21) Appl. No.: 10/945,649

(22) Filed: Sep. 21, 2004

(65) Prior Publication Data

US 2006/0062353 A1    Mar. 23, 2006

(51) Int. Cl.
*G21K 1/00* (2006.01)
*G21K 3/00* (2006.01)
*H05G 1/64* (2006.01)

(52) U.S. Cl. .................. 378/145; 378/158; 378/98.9
(58) Field of Classification Search ............... 378/16, 378/19, 98.7, 98.8, 145, 147–153, 156–159
See application file for complete search history.

(56) References Cited

U.S. PATENT DOCUMENTS

| | | | |
|---|---|---|---|
| 3,755,672 A | | 8/1973 | Edholm et al. |
| 4,347,440 A | | 8/1982 | Haas |
| 4,497,062 A | | 1/1985 | Mistretta et al. |
| 4,868,857 A | | 9/1989 | Dobbins, III |
| 5,081,659 A | | 1/1992 | Dobbins, III |
| 5,107,529 A | | 4/1992 | Boone |
| 5,185,775 A | | 2/1993 | Sirvin |
| 5,237,598 A | * | 8/1993 | Albert ..................... 378/98.6 |
| 5,267,296 A | * | 11/1993 | Albert ..................... 378/113 |
| 5,625,665 A | | 4/1997 | Fokkink et al. |

(Continued)

FOREIGN PATENT DOCUMENTS

WO    WO 98/27867    7/1998

OTHER PUBLICATIONS

"Abstract: Effect of Area X-ray Beam Equalization on Image Quality and Dose in Digital Mammography", 1992.

(Continued)

*Primary Examiner*—Edward J. Glick
*Assistant Examiner*—Irakli Kiknadze
(74) *Attorney, Agent, or Firm*—McAndrews, Held & Malloy, Ltd.; Peter J. Vogel; Michael A. Della Penna

(57) ABSTRACT

The present invention provides for an x-ray system and method using dynamic automated spatial modulation of an x-ray beam. The system includes an x-ray source transmitting a spatially modulated beam towards an object to be imaged, an x-ray detector receiving the beam and measuring a plurality of intensities across the beam, a beam processor controlling the beam intensity profile, and an image processor producing an output image signal. The detector produces a residual image based on at least the intensities measured at the detector. The beam intensity profile may be based on at least some of the following: (a) the residual image from the x-ray detector, (b) current beam intensities, (c) regions on interest in the image, and (d) predicted or measured object motion in the image. The system's output image is based on one or more of said residual image and said beam intensity signal.

48 Claims, 11 Drawing Sheets

U.S. PATENT DOCUMENTS

| | | | |
|---|---|---|---|
| 5,778,046 | A | 7/1998 | Molloi et al. |
| 5,878,111 | A | 3/1999 | Schulz |
| 5,881,127 | A | 3/1999 | Molloi et al. |
| 6,055,295 | A | 4/2000 | Murthy et al. |
| 6,108,403 | A | 8/2000 | Cooper, III et al. |
| 6,201,852 | B1 | 3/2001 | Goddu et al. |
| 6,453,012 | B2 | 9/2002 | Herbert |
| 6,480,570 | B1 | 11/2002 | Ikeda |
| 6,501,828 | B1 * | 12/2002 | Popescu .................. 378/150 |

OTHER PUBLICATIONS

"Advanced Multiple Beam Equalization Radiography (Amber)", available at http://www.amershamhealth.com/medcyclopaedia/medical volume%201/ADVANCED%20MULTIPLE%20BEAM%20EQUALIZATION%20RADIOGRAPHY%20%20AMBER%20.ASP (last visited Jul. 20, 2004).

"Computer Equalization Radiography", available at http://www.amershamhealth.com/medcyclopaedia/medical/volume%20V%201/COMPUTED%20EQUALIZATION%20RADIOGRAPHY.ASP (last visited Jul. 20, 2004).

"X-ray Area Beam Equalization", Univ. of Cal. Radiological Sciences, available at http://saturn.radsci.uci.edu/research/equalization/equalization.html, last visited Jul. 20, 2004.

Digiray Digital X-ray Systems Technical Specifications, available at http://www.digiray.com/specs.htm, last visited Jul. 20, 2004.

Boone et al., "Filter Wheel Equalization for Chest Radiography : A Computer Simulation", Med. Phys. 22 (7), Jul. 1995, Am. Assoc. Phys. Med., pp. 1029-1037.

Edholm et al., "Primary X-Ray Dodging," Radiology, vol. 99, Jun. 1971, pp. 694-696.

Geluk, "Abstract: Digital Equalization Radiology", Proceedings of SPIE, vol. 3659, Medical Imaging 1999: Physics of Medical Imaging, May 1999, pp. 471-477.

Hasegawa et al., "Digital Beam Attenuator Technique for Compensated Chest Radiography", Radiology, vol. 159, No. 2, pp. 537-543.

Hasegawa et al., "Geometrical properties of a digital beam attenuator system", Med. Phys. 14: 3, pp. 314-321, May-Jun. 1987.

Kruger et al., "A Digital Video Image Processor for Real-Time X-Ray Subtraction Imaging", Optical Engineering, vol. 17, No. 6, Nov.-Dec. 1978, pp. 652-657.

Kusoffsky et al., "Attenuation Equalizing Filter in Diagnostic Radiography," Acta Radiologica Therapy Physics Biology 15, Jun. 1976, pp. 259-272.

Molloi et al., "Abstract: X-ray Beam Equalization for Digital Fluoroscopy", Proceedings of SPIE, vol. 2708, Medical Imaging 1996: Physics of Medical Imaging, Apr. 1996, pp. 167-178.

Molloi et al., "Area X-ray Beam Equalization for Digital Angiography", Med. Phys. 26 (12), Dec. 1999, Am. Assoc. Phys. Med., pp. 2684-2692.

Peppler et al., "Digitally Controlled Beam Attenuator", SPIE, vol. 347, Application of Optical Instrumentation in Medicine, 1982, pp. 106-111.

Pizer et al., "Adaptive Histogram Equalization and Its Variations", Computer Vision, Graphics and Image Processing 39, 1987, pp. 355-368.

Plewes et al., "Improved Lung Nodule Detection with an Equalized Image", SPIE, vol. 233, Application of Optical Instrumentation in Medicine VIII, 1980, pp. 183-189.

Plewes, "A Scanning System for Chest Radiography with Regional Exposure Control: Theoretical Considerations", Medical Physics, vol. 10, No. 5, Sep./Oct. 1983.

Rudin et al., "Region of Interest Fluoroscopy", J. of Med. Phys., Sep.-Oct. 1992; 19(5), pp. 1183-1189.

Stoel et al., "Abstract : Computer-related Multiple Beam Equalization: Image Processing Algorithm and Research Tool for AMBER", Proceedings of SPIE, vol. 1896, Medical Imaging 1993; Physics of Medical Imaging, Sep. 1993, pp. 236-245.

Vlasbloem, et al., "AMBER: A Scanning Multiple-Beam Equalization System for Chest Radiography", Radiology, vol. 169, No. 1, pp. 29-34.

International Search Report for EP 05255494.6 (Feb. 17, 2006).

* cited by examiner

SYSTEM AND METHOD FOR AN ADAPTIVE MORPHOLOGY X-RAY BEAM IN AN X-RAY SYSTEM

BACKGROUND OF THE INVENTION

The present invention generally relates to an x-ray imaging system. In particular, the present invention relates to a system and method for x-ray imaging with spatial modulation of the x-ray beam.

Conventional x-ray imaging systems consist of an x-ray source exposing an object to an essentially uniform x-ray beam. As the beam passes through the object, varying radiographic densities throughout the object cause varying portions of x-ray flux to be attenuated (for example, absorbed or scattered) in the object. After passing through the object, the remaining beam strikes a detector. As the detector receives the beam with varying intensities, the detector measures and communicates the beam intensities to a data acquisition system. The data acquisition system may then use the beam intensities to create a shadow image.

Several fundamental problems exist in this conventional approach. For example, the entirety of the imaged object receives a relatively high x-ray dose independently of varying radiographic thicknesses throughout the object, regardless of the presence of motion in imaged objects and/or the degree to which various object volumes are of interest to the viewer.

A large dose is commonly used to ensure that the object volumes that attenuate the largest amount of the beam receive sufficient photon flux to provide an image of those volumes. If a beam striking an object volume with a large radiographic thickness has insufficient intensity to allow a sufficient number of x-ray photons to reach the detector, then the resultant shadow image may not produce sufficient contrast for features in the object volume. A sufficient number of photons must reach the detector to allow differentiating objects' radiographic thickness variations from fluctuations in the detected numbers of photons. These fluctuations are known as quantum noise or mottle.

However, the high x-ray doses also strike object volumes with smaller radiographic thicknesses, which require much less dose to be imaged adequately. Excessive exposures of the thin object volumes may be harmful. In addition they may cause additional imaging problems, such as, for example, (a) increased x-ray scatter, (b) increased veiling glare, and (c) detector saturation. Current high-performance x-ray detectors may allow imaging object volumes with both large and small radiographic thicknesses without saturation. However, such systems may still expose object volumes with smaller radiographic densities to unnecessarily large x-ray doses. In addition, such high-performance detectors add considerable expense to an x-ray system.

Another problem with conventional x-ray imaging are high doses to object volumes imaged for reference only without the need for high spatial and grayscale resolution. These volumes may be imaged with a decreased dose rate and still provide adequate information while object volumes that require high grayscale and spatial resolutions may still need to be exposed to usual doses.

Another problem with conventional fluoroscopy is excessive exposure rates to object volumes where little change occurs from frame to frame and, therefore, little new information is present. If an image region is known to contain little object motion, it may be possible to reduce dose and increase information reuse from previous frames to render an accurate representation of the object. Moving or changing object volumes may still need to be exposed to regular dose rates to provide adequate image quality.

Several beam modulation techniques have already been proposed. These techniques may be classified into two general categories based on the goals they pursue: (a) Beam Equalization methods attempt to equalize or homogenize the detector exposure spatially; and (b) Region-of-Interest Radiography and Fluoroscopy methods attempt to reduce exposure to anatomical volumes of lesser clinical interest. Some examples of each will be given below.

Another categorization of beam modulation methods is based on whether or not the displayed image is compensated for the introduced brightness modulation. In many applications this compensation is unnecessary as the uncompensated images are of equal or greater value to the user as the uncompensated images. In other applications, it may be necessary to present image intensities that accurately represent true radiographic thicknesses in the imaged objects and, before presenting the output image, the system may need to reverse the intensity variation introduced into the x-ray beam.

Beam modulation methods may also be categorized based on whether the beam modulation is configured and invoked automatically or manually. Thus, automatic and manual beam modulation methods are distinguished.

Several techniques have been proposed to equalize or make uniform the exposure to the x-ray detector for the purpose of dose reduction, x-ray scatter reduction, or to prevent detector saturation. These techniques typically consist of placing an equalizing beam filter between the x-ray source and imaged objects. For example, in Sirvin, U.S. Pat. No. 5,185,775, entitled "X-ray Apparatus Including a Homogenizing Filter", a filter matching the morphology of the imaged object is placed between the x-ray source and the imaged object to homogenize detector exposure and to improve the quality of angiographic images.

Several technologies have been proposed to quickly produce filters matching the morphology of arbitrary objects. One such technology is disclosed in Boone, U.S. Pat. No. 5,107,529, entitled "Radiographic Equalization Apparatus and Method." Boone describes the utilization of a plurality of juxtaposed discs used in the filtration of an x-ray beam. Each disc includes a complex attenuation pattern and is individually rotatable in order to obtain numerous attenuation patterns. Based on a single scout image, discs are rotated so as to create an optimal attenuation pattern. The attenuation pattern provides for increased beam attenuation in areas of the imaged object corresponding to overexposed areas of the preliminary image. In this way, Boone describes an x-ray filtering apparatus and method for equalizing x-ray beam intensity received at a detector.

Another proposed solution is disclosed in Edholm et al., U.S. Pat. No. 3,755,672, entitled "Exposure Compensating Device for Radiographic Apparatus." Edholm describes an x-ray filter that may alter an amount of x-ray absorption. The filter has a variable shape such that the amount of x-ray absorption within different portions of the filter can be independently altered. In addition, the amounts of x-ray absorption in portions of the filter are automatically adjusted in response to signals based on a preliminary or scout image detected by radiation detecting means located below the imaging plane. Edholm therefore describes an x-ray filter that can automatically alter an amount of x-ray attenuation based on x-ray intensities detected during a preliminary image.

Another proposed solution is disclosed in Dobbins, III, U.S. Pat. Nos. 4,868,857 and 5,081,659, entitled "Variable Compensation Method and Apparatus for Radiological Images." Dobbins describes the modulation of an x-ray beam based on a preliminary or scout low-dose x-ray image. As above with regards to Boone and Edholm, Dobbins therefore describes a static x-ray filtration method and apparatus. The modulation is based on a digital beam attenuator mask that provides for an x-ray beam that is equalized when received at the detector. The digital beam attenuated mask of Dobbins is combined digitally with detected x-ray intensities to form a final x-ray image.

Region-of-Interest Fluoroscopy ("ROIF") has been proposed to address the problem of excessive exposures to less important object volumes (e.g. Rudin et al, "Region of Interest Fluoroscopy", J. of Med. Phys., 1992 September-October; 19(5):pp. 1183-9). In ROIF, a procedure-specific filter is placed between the x-ray source and the imaged object to selectively attenuate the x-ray beam in regions of lesser clinical interest. Prior to the procedure, compensating mask images are acquired by taking an image of the attenuating filter alone. During the procedure, the mask image is subtracted digitally, similarly to digital subtraction angiography techniques, to recover true attenuations of the imaged object.

Many of the proposed systems require human intervention to produce or select beam filters, to position them in the beam, and to perform image compensation. Several solutions have been proposed to automate portions or the entirety of the beam equalization process. These solutions collectively are known as Computed Equalization Radiography. Some categories of such solutions are: (a) scanning or raster systems (e.g. Vlasbloem et al, "AMBER: A Scanning Multiple-Beam Equalization System for Chest Radiography", Radiology, vol. 169, No. 1, pp. 29-34), (b) solutions using x-ray absorbing liquids or deformable substances whose volumetric shapes are controlled mechanically or electronically (e.g. Tang, Mather and Zhou, "Area x-ray beam equalization for digital angiography", J. of Med. Phys., 1999, 26(12):pp. 2684-92), (c), printing desired attenuation patterns with x-ray absorbing ink, (Hasegawa et al., "Geometrical properties of a digital beam attenuator system", Med. Phys. 14: 3, 314-21, May-June, 1987) (d) solutions that use multi-leaf or multi-layer semitransparent filters of varying thickness whose positions are adjusted independently to produce desired attenuation patterns (e.g. Boone, U.S. Pat. No. 5,107,529, entitled "Radiographic Equalization Apparatus and Method").

The above references describe beam modulation techniques, in which the required x-ray intensity field is computed from a preliminary scout image or is programmed manually. However, as many x-ray procedures may require hundreds or thousands of continuous frames from multiple views, these solutions do not provide a mechanism for uninterruptible point-and-shoot imaging with optimized beam modulation.

Some of the proposed solutions such as raster-beam or slit-beam scanning systems (such as AMBER) significantly increase x-ray tube loading requirements because only a small portion of the x-ray beam is used at any time.

Solutions that use semitransparent substances to selectively attenuate the beam are sensitive to the photon energies in the x-ray beam. Filters designed to attenuate the x-ray beam with effective x-ray photon energies around 35 keV would be too opaque for meaningful beam modulation when the effective photon energy is dropped to, for example, 20 keV, or too transparent when the effective photon energy is increased to, for example, 70 keV. Addressing the problem with specialized filters that work with low- and high-energy beams would require a substantial increase in the complexity of such systems. The amounts or thicknesses of these x-ray absorbing substances would need to vary by significant factors when the x-ray technique undergoes a significant change. For such systems to provide meaningful beam modulating factors in a wide range of x-ray techniques, their designs may be prohibitively complex.

In addition, automated beam modulation systems proposed in above references may be too bulky, slow, and expensive to provide high speed, resolution, and dynamic range that would make them useful in a wide spectrum of imaging applications.

To make a beam modulation system useful in dynamic imaging environments such as medical interventional imaging, a need exists for an improved system and method allowing for modulation of an x-ray beam continuously without user intervention and without the need for a scout shot. Such a system and method can control the x-ray beam intensities across the field of view prior to the x-ray beam striking the imaged object. The degree of variation may need to be sufficiently high, for example, up to one or two orders of magnitude while resolving a sufficient number of intermediate intensity values in a wide range of x-ray techniques. The system and method may also automatically reduce the x-ray exposure to regions of an imaged object where a lower dose is sufficient to adequately render features of interest, such as in radiographically thin, static, or less interesting regions, for example. The system may also render the displayed image without compromising various aspects of image quality, distracting the viewer, or distorting displayed images. In short, such system can deliver the benefits of beam equalization and region-of-interest fluoroscopy (for example, reduced dose, reduced x-ray scatter, reduced optical glare, and reduced saturation) while making the displayed images appear as if produced with a uniform high-exposure beam. In addition, such a system and method can provide for improved image quality by irradiating with higher doses object volumes of interest, object volumes with high radiographic thickness, and object volumes with anticipated motion.

BRIEF SUMMARY OF THE INVENTION

The present invention provides for an x-ray system using spatial modulation of an x-ray beam and subsequent digital removal of brightness or noise distortions introduced by beam modulation from the output image. The system includes an x-ray source, an x-ray detector, a beam processor and an image processor. The source transmits an x-ray beam towards an object to be imaged. The beam includes a beam intensity field based on at least a beam intensity signal. The detector receives the beam and measures a plurality of intensities of the beam. The detector also produces a residual image signal based on at least the measured intensities. The beam processor updates the beam intensity signal continually or periodically to maintain an optimal beam intensity field. The image processor produces an output image signal based on one or more of the residual image signal and the beam intensity signal.

The present invention also provides for a method of x-ray imaging with spatial modulation of an x-ray beam. The method includes transmitting a spatially modulated x-ray beam towards an object to be imaged, receiving the beam at an x-ray detector, measuring a plurality of beam intensities at the detector, creating a residual image signal based on at least the measured intensities, and producing an output image signal. The x-ray intensities across the initial beam are caused to vary spatially based on at least a beam intensity signal. The beam intensity signal is based on, at least, some of the following: (a) measured or predicted radiographic thicknesses in imaged objects, which, in turn, may be determined from the current residual image and the beam intensity field, (b) measured or predicted radiographic thicknesses in imaged objects, and (c) detected or predicted object motion. The output image signal is based on one or more of the residual image signal and the beam intensity signal.

The present invention also provides for a system and method for "x-ray dodging," a technique for automatic and dynamic spatial modulation of an x-ray beam based on a beam intensity signal. X-ray dodging consists of placing arrangements of x-ray-blocking elements in the beam. Some of the elements may overlap to various degrees thus varying the areas of the blocked portions of the beam. The entire arrangement is then caused to undergo a high-frequency periodic motion while the beam intensity is caused to vary in time in synchronization with the periodic motion. The combined effect of this process smoothens the blocked portions of the beam to result in a continuously varying smooth semitransparent attenuations pattern with a high number and range of gradation levels.

Figure 1:
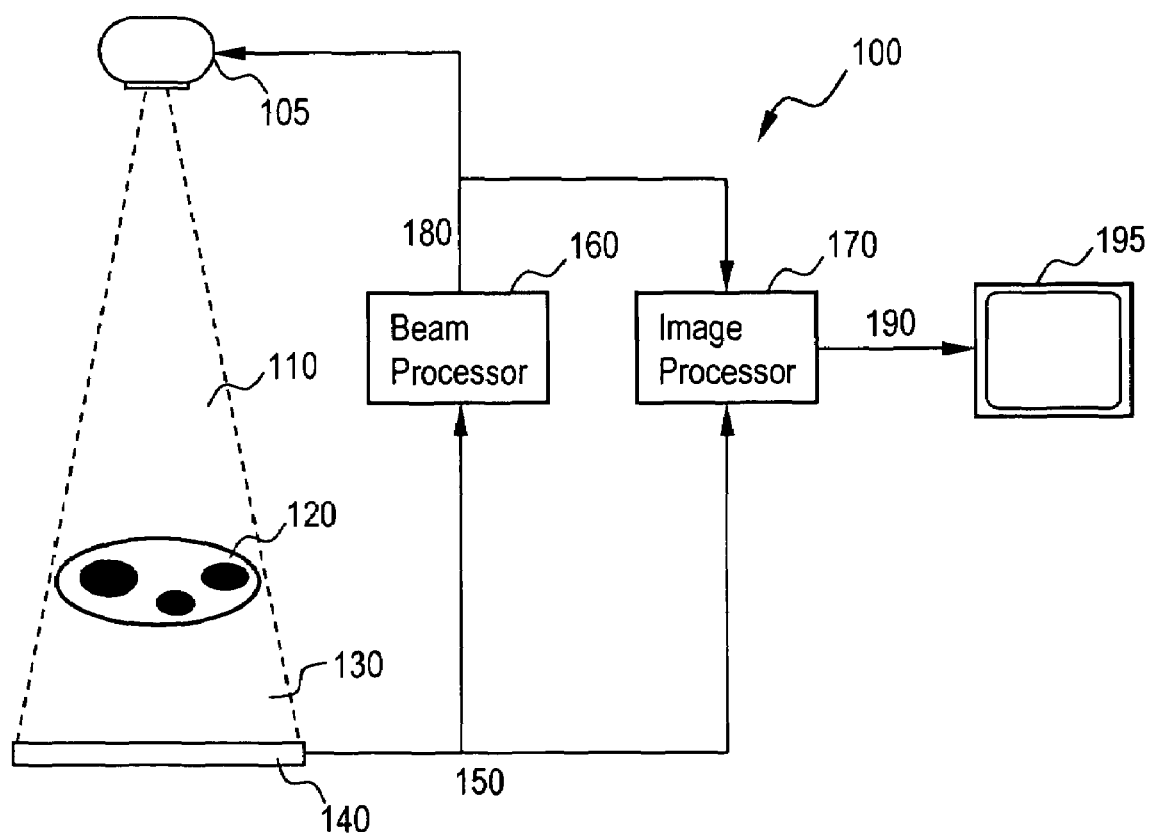
FIG. 1 illustrates a schematic diagram on an x-ray system using x-ray beam modulation in accordance with an embodiment of the present invention.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

FIG. 1 illustrates a schematic diagram on an x-ray system 100 using x-ray beam modulation in accordance with an embodiment of the present invention. System 100 includes an x-ray source 105 producing a spatially modulated beam 110, an imaged object 120, an x-ray detector 140, an x-ray beam processor 160, an image processor 170, and a display device 195. Modulated beam 110 passes through imaged object 120, is attenuated to various degrees by its features, and forms residual beam 130. Detector 140 measures the beam intensities in the residual beam 130 and communicates a residual image 150 to the beam processor 160 and the image processor 170. A beam intensity signal 180 can be communicated from the beam processor 160 to the x-ray source 105 and to the image processor 170. The image processor produces a displayed image signal 190 and communicates to display device 195.

As mentioned above, source 105 is capable of transmitting a spatially modulated beam 110 towards imaged object 120. More specifically, source 105 may be capable of altering x-ray intensities across beam 110 non-uniformly according to a beam intensity signal. A beam intensity signal is a digital representation of the intensity field of a spatially modulated x-ray beam 110.

Source 105 may be capable of altering the x-ray intensity field in beam 110 by any one of several embodiments. For example, system 100 may use a raster beam 110 by moving a narrow beam 110 back and forth in a raster pattern over particular areas of object 120 while varying the beam's intensity temporally and integrating the image in the detector 140. In another embodiment, source 105 may include multiple beam sources, each exposing different portions of imaged object 120. Source 105 may then modulate beam 110 spatially by controlling the outputs of individual x-ray sources.

A spatially modulated x-ray beam 110 may be constructed to match a distribution of radiographic thicknesses of object 120. For example, object 120 may have a known, measured, or anticipated distribution of thickness (for example, based on previous frames in a fluoroscopic sequence). Based at least on this distribution, a beam intensity signal may be created to increase the exposure to radiographically thick regions and/or decrease exposure to radiographically thin regions of imaged object 120, thereby possibly resulting in the approximate equalization of intensities in residual beam 130, for example. Residual beam 130 can include an x-ray beam after it has been attenuated by at least imaged object 120, for example.

A spatially modulated x-ray beam 110 may be constructed to match a distribution of region on interest in object 120. Regions of interest may be areas or volumes in object 120 that a user of system 100 desires to image. Regions of interest in object 120 may be known a priori from previous scans or general atlases, programmed, inferred, or anticipated. Based on at least the distribution of these regions of interest, a beam intensity signal may be created that results in increased x-ray exposures to regions of great interest and/or decrease x-ray exposures to regions of lesser interest, for example.

A spatially modulated x-ray beam 110 may also be established to match a distribution of regions of sustained motion in object 120. Object 120 may have regions or volumes that are likely to move relative to imaging system 100. Other regions are more likely to remain static. For example, if object 120 is a chest cavity of a human patient, it may include the patient's heart moving relative to the rest of the chest cavity. Regions of motion in object 120 may be programmed by users, known a priori, measured, or anticipated. Less exposure is necessary in regions with little motion where image processing techniques may be employed to reuse information from earlier frames to produce a high-quality representation of these static regions. Based on at least the anticipated distribution of motion, a beam intensity signal may be created that results in increased x-ray exposures to regions with motion and/or decreased x-ray exposures to regions with little or no motion.

Finally, a spatially modulated x-ray beam 110 may be established to match a combination of the three distributions described above, for example, (a) radiographic thicknesses, (b) regions of interests, and (c) regions of object motion may be combined to produce an improved beam intensity signal.

Once beam 110 passes through object 120, detector 140 receives residual beam 130. Detector 140 is a device capable of measuring or recording the intensity pattern projected by residual image 130. For example, detector 140 may be a solid-state x-ray detector, or an image intensifier coupled with a charged-coupled device digital video camera.

Based at least on measured intensities in residual beam 130, detector 140 may create residual image 150. For example, residual image 150 may comprise electronic data representing various residual beam 130 intensities received by detector 140. Detector 140 communicates residual image 150 to at least one of beam processor 160 and image processor 170.

Beam processor 160 is an image-processing component of system 100. Beam processor 160 may be any processor capable of receiving residual image 150 from detector 140, creating beam intensity signal 180, and communicating beam intensity signal 180 to at least one of source 105 and image processor 170. Beam processor 160 may be embodied in a computer general-purpose microprocessor, a software component, or a specialized digital signal processing ("DSP") circuit, for example. Beam processor 160 may be embedded in a system supplying processing for system 100, which may also perform additional tasks for system 100, such as those performed by image processor 170.

After beam processor 160 receives residual image 150, beam processor 150 examines residual image 150 to determine how the beam intensity signal 180 needs to be modified. Thus beam processor 160 completes a feedback loop that may periodically or continuously update the beam 110 intensity field based at least on changes in imaged object 120. Because beam processor 160 may "know" what beam 110 intensity field was applied to produce the received residual image 130, beam processor 160 may not require a uniform-beam scout shot to estimate radiographic thicknesses in imaged object 120 and may further be capable of periodically and/or continually updating beam intensity signal 180 as imaged object 120 moves or changes throughout an imaging session.

When beam intensity signal 180 is based primarily on radiographic thicknesses in imaged object 120, the feedback loop may result in residual image 130 being essentially uniform, within the beam-modulating performance limitations of x-ray source 105. This is to say that in some cases, the spatial resolution limitations, the dynamic range limitations, or grayscale resolution limitations of the beam modulation in x-ray source 105 will not allow complete equalization of the beam, even though a significant improvement may be produced thanks to partial equalization. These limits include spatial resolution, intensity resolution, and dynamic range. The residual image can include information of object movement or other changes as well as detail that is not resolved by the beam modulator in x-ray source 105. If the beam modulation capabilities of x-ray source 105 approach corresponding image acquisition capabilities of x-ray detector 140, then residual image 140 may only include noise and motion, if any. Thus, considerable useful information about imaged object may be included in beam intensity signal 180.

When beam intensity signal 180 is also based on anticipated regions of motion and regions of interest in object 120, then beam processor 160 may create a beam intensity signal 180 to cause increased beam intensity in these regions. The residual image 140 may therefore be non-uniform and may not accurately represent radiographic thicknesses in imaged object 120.

As described above, beam processor 160 may also communicate beam intensity signal 180 to image processor 170. Image processor 170 may be any processor capable of combining two or more image signals into a third image signal using image algebra operators. For example, image processor 170 may be a specialized hardware component, a programmable device, or an embedded software component running on a general-purpose microprocessor, for example.

Image processor 170 subtracts beam intensity signal 180 from residual image 150 to create output image 190. This subtraction may occur, for example, on a pixel-for-pixel basis. The specific meaning of the subtraction operation depends on the grayscale transforms applied to constituent images. For example, if a logarithmic grayscale transform has been applied to the residual image and to the beam intensity signal, then a simple arithmetic subtraction may be used. Combined image 190 may then accurately represent true radiographic thickness in object 120, as if acquired with a uniform x-ray beam, for example. Signal delays may need to be built into the system to ensure that beam intensity signals 180 are combined with matching residual images 150.

Image processor 170 may also adapt its processing in accordance to the same region-of-interest information and region-of-motion information used to produce the beam intensity signal 180 in beam processor 160. These adaptations may include spatial filtration, temporal filtration, feature enhancements, noise suppression, and others. For example, when beam processor 160 causes a dose reduction to a region of lesser interest, image processor 170 may increase noise reduction in corresponding image regions. As another example, when beam processor 160 causes a dose reduction to a region where little object motion is anticipated, then increased temporal filtration may be used to increase the reuse of previous frames to present a high-quality image. Multiscale image processing schemes may facilitate these solutions.

Figure 11:
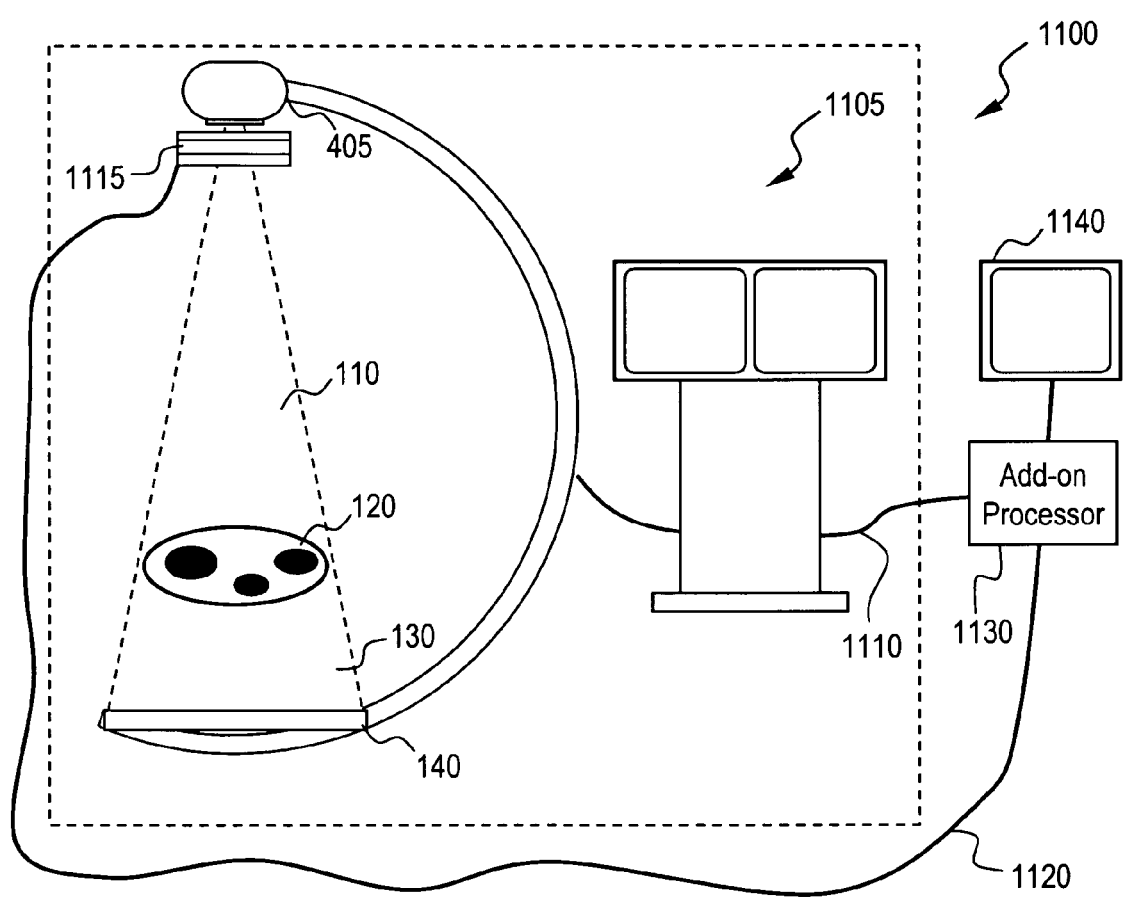
FIG. 11 illustrates an add-on beam modulation system 1100 that works in combination with a conventional fluoroscopic imaging system 1105 used in accordance with an embodiment of the present invention.

In another embodiment of the present invention, the present invention may be embodied as an external add-on device to an existing imaging system. In FIG. 11, system 1100 includes an existing conventional system 1105, demarcated by a dash-lined box, which, in turn, includes an x-ray source 405 and an x-ray detector 140. An external beam-modulating device comprises an external add-on processor 1130, a beam modulator 1115, and a display device 1140. The conventional system's video output 1110 is connected to the add-on processor 1130. The beam modulator 1115 is attached to the conventional system's 1115 x-ray source 405. The add-on processor 1130 plays the roles of the beam processor 160 and image processor 170 as in FIG. 4. The beam configuration signal 420 is conveyed to the beam modulation 1115 along the modulator connection 1120. The video signal 1110 conveys residual image signal to add-on processor 1130.

A conventional digital fluoroscopy x-ray imaging system typically includes x-ray source 105, detector 140, and is capable of producing a video output signal 1110. In operation, source 105 transmits an x-ray beam 110 towards object 120. After beam 110 passes through object 120 and becomes residual beam 130 (as described above), detector 140 measures the x-ray intensities of residual beam 130. The system 1105 then converts this residual beam into a video signal 1110 which may be fed into other systems.

However, in this embodiment, external beam modulation device 1115 may be added to such system to add the functionality of the present invention to an existing imaging system. Device 1115 is controlled by an add-on processor 1130.

In operation, processing block received video output 1110 from the conventional system 1105. Add-on processor 1130 then acts to achieve the same functionality of the beam processor 160 and image processor 170, as described above. For example, once add-on processor 1130 receives residual image 1110, a beam processor similar to beam processor 160 examines residual image video signal 1120 to determine how a beam intensities in beam 110 need to be modified. The beam processor of add-on processor 1130 completes a feedback loop that may periodically or continuously update the beam 110 intensity field based at least on changes in imaged object 120, as described above. Device 1120 may then communicate the beam intensity signal 180 to beam modulator via the beam modulator connection 1120.

In addition, once the beam processor of add-on processor 1130 determines a beam intensity signal, add-on processor 1130 may also communicate the beam intensity signal to an internal image processor similar to image processor 170 of system 100. The image processor of add-on 1130 then subtracts beam intensity signal 180 from residual image 150 to create output image 190. This subtraction may occur, for example, on a pixel-for-pixel basis. Device 1120 can then communicate the image 190 to an external display device 1140 for display to a user of system 1100. Therefore, the presently described embodiment provides for the simple addition of a beam modulation device 1120 to an existing x-ray imaging system in order to achieve the functionality of the present invention.

Figure 2:
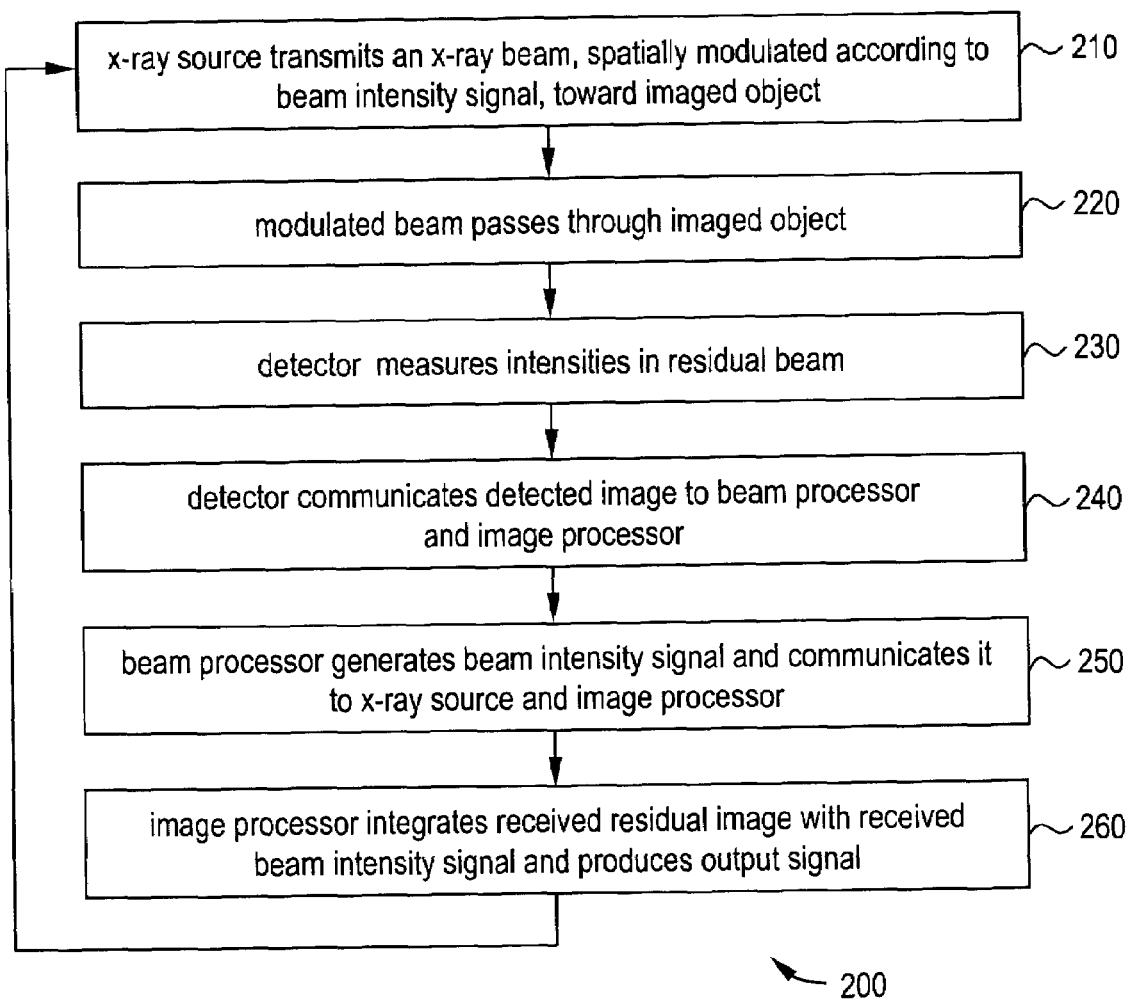
FIG. 2 illustrates a flowchart according to a method of generating an output image signal based on the above described feedback loop according to an embodiment of the present invention.

FIG. 2 illustrates a flowchart according to a method 200 of generating an output image signal 190 based on the above described feedback loop according to an embodiment of the present invention. First, at step 210, an x-ray source 105 transmits an x-ray beam 110 towards an object 120. Next, at step 220, the spatially modulated beam 110 passes through and is attenuated by the object 120. The resultant beam that exists the other side of the object 120 is a residual beam 130. At step 230, a detector 140 measures x-ray intensities in the residual beam 130 in order to create a residual image 150. Next, at step 240, the detector 140 communicates the residual image 150 to a beam processor 160 and an image processor 170. Next, at step 250, the beam processor 160 generates a beam intensity signal 180 and communicates signal 180 to the source 105 and image processor 170. Next, at step 260, the image processor 170 integrates the residual image 150 with the beam intensity signal 180 in order to produce an image output signal 190. This output signal 190 may then be displayed on a display device 195, for example. Next, method 200 may proceed back to step 210. In this way, method 200 may proceed in a feedback loop manner.

The beam processor 160 may create and communicate beam intensity signal 180 on a regularly repeated or continuous basis such as fluoroscopic frame rates of 30, 15, or 7.5 frames per second.

In addition to combing the two constituents into the output image, beam processor 170 may also perform other image processing tasks such as feature enhancement, dynamic range suppression, noise reduction, digital subtraction angiography ("DSA"), and grayscale transformations, for example. These processing tasks in image processor 170 may be correlated with beam modulating tasks in beam processor 160. For example, regions that are not anticipated to contain motion may receive reduced x-ray exposures, as controlled by beam processor 160, but they may also be more heavily temporally averaged to reduce image noise in image processor 170. As another example, regions of lesser interest may receive reduced x-ray exposures but may also be more spatially averaged to reduce noise in image processor 170, for example.

Display device 195 receives output image 190 from image processor 170 and presents it to a viewer.

Figure 3:
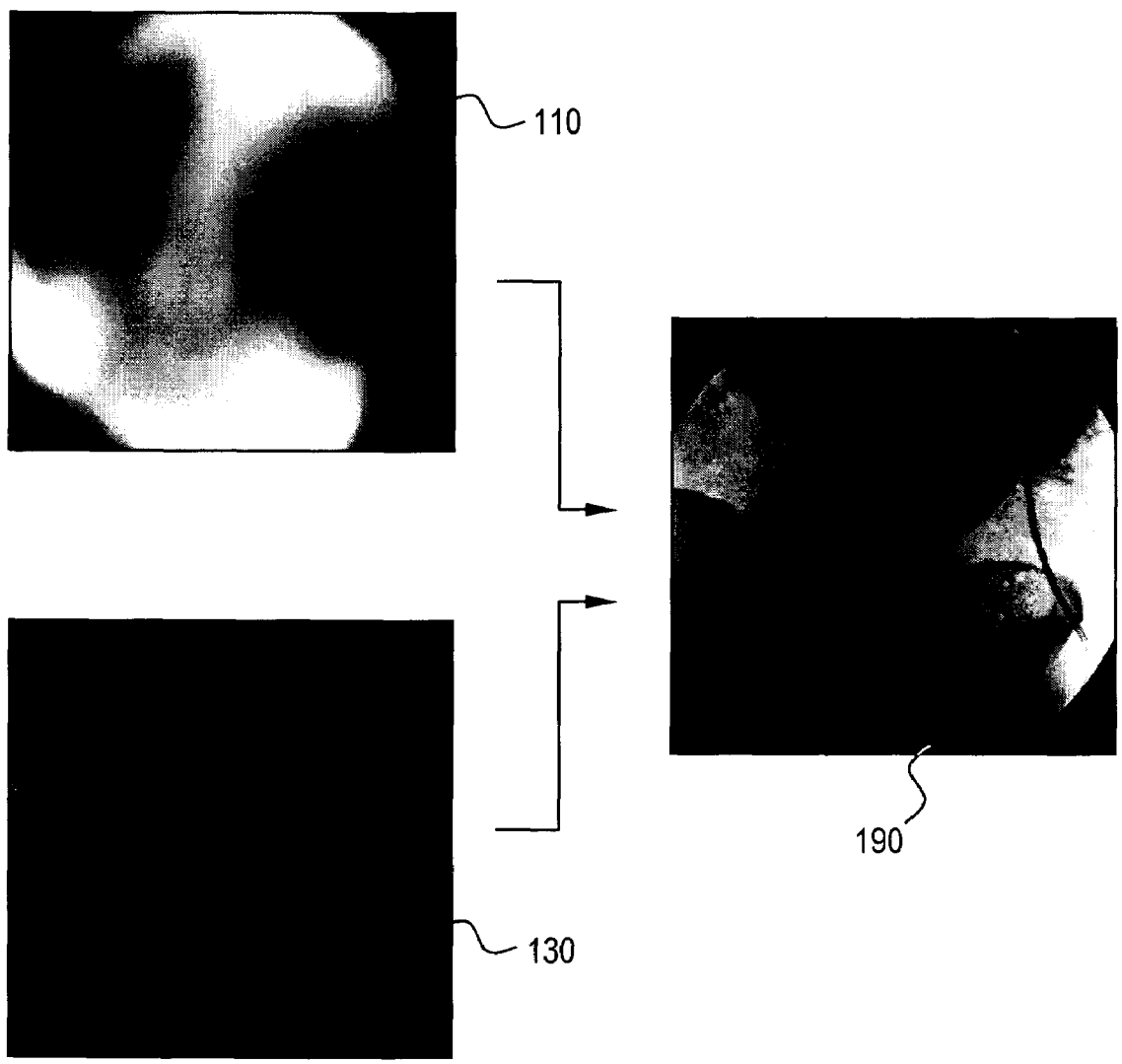
FIG. 3 illustrates examples of beam intensity field according to an embodiment of the present invention

FIG. 3 illustrates examples of spatially modulated beam 10 according to an embodiment of the present invention, residual image 150, and displayed image signal 190 after the feedback loop has produced a near-optimal beam intensity field. In FIG. 3, the beam processor is programmed to equalize the residual image without consideration for regions of interest or anticipated object motion. In addition, the spatial resolution of the beam modulator is limited in FIG. 3, so the beam intensity signal comprises only the low-frequency image information and the residual image contains the remaining high-frequency image information. The combined output image 190 appears as if acquired with a uniform-beam system at a high dose and high resolution, when, in fact, the averaged dose to the imaged object is significantly reduced.

Figure 4:
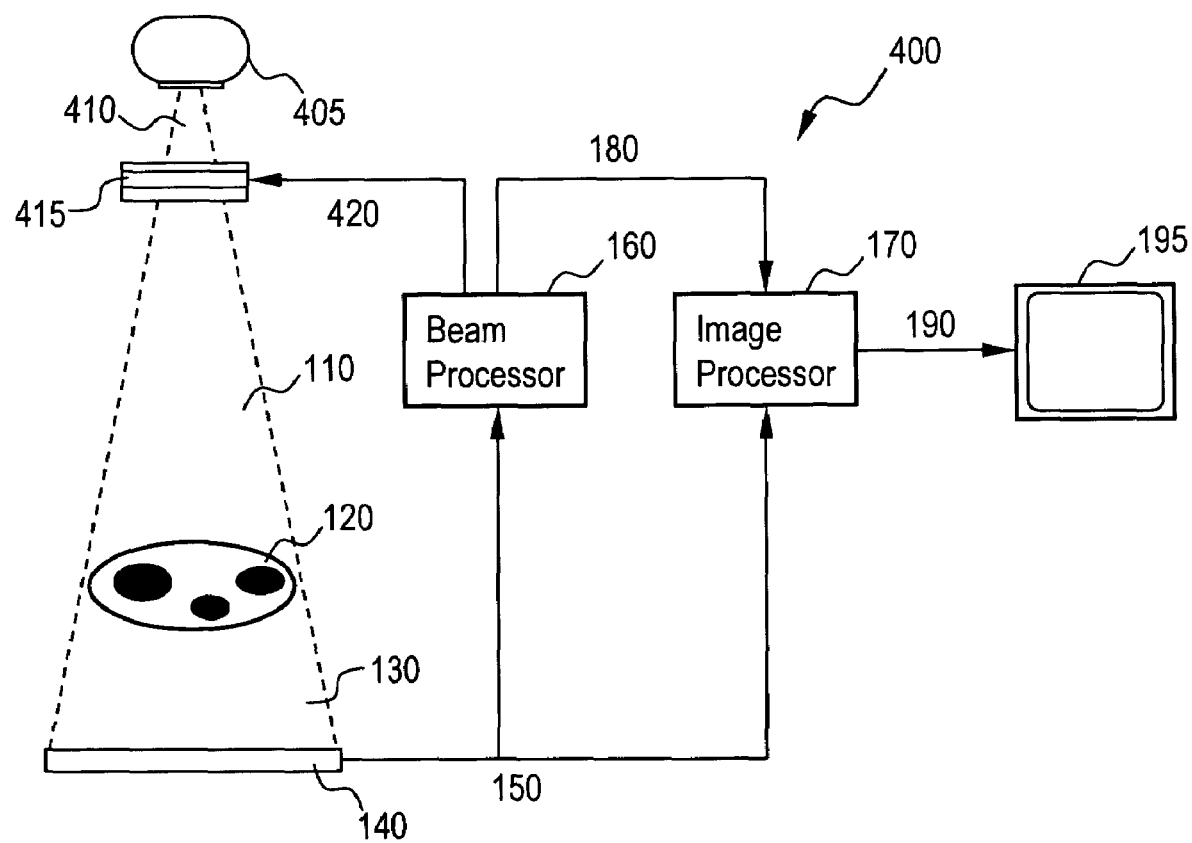
FIG. 4 illustrates a schematic diagram of an x-ray system using spatial modulation of x-ray beam used in accordance with an embodiment of the present invention.

FIG. 4 illustrates a schematic diagram of an x-ray system 400 using spatial modulation of x-ray beam 110 used in accordance with an embodiment of the present invention. System 400 includes an x-ray source 405 emitting an essentially uniform x-ray beam 410, a beam-modulating filter 415, an imaged object 120, an x-ray detector 140, a beam processor 160, an image processor 170, and a display device 195. The initial beam 410 may not be completely uniform due to the Heel effect, for example. Beam modulating filter 415 is placed between x-ray source 405 and imaged object 120. X-ray source 405 transmits an essentially uniform x-ray beam 410 toward modulating filter 415, imaged object 120, and detector 140. At least some portion of uniform beam 410 passes through modulating filter 415 to form modulated beam 110. Modulated beam 110 passes through imaged object 120, is attenuated to various degrees by its features, and forms residual beam 130. X-ray detector 140 measures intensities in residual beam 130, forms the residual image 150 and communicates it to beam processor 160 and image processor 170. The beam processor 160 forms the beam intensity signal 180 and communicates the signal 180 to the image processor 170. The beam processor 160 then translates the beam intensity signal 180 into a modulator configuration signal 420 and communicates it to the beam-modulating filter 415. In this way, both the beam intensity signal 180 and the modulator configuration signal 420 act to determine the spatial modulation of an x-ray beam. The image processor 170 creates output image 190 and communicates it to display device 195. Image processor 170 may create output image 190 by integrating intensity signal 180 and modulator configuration signal 420, similar to as described above in regards to FIG. 1.

Beam-modulating filter 415 may attenuate initial beam 410 according to modulator configuration signal 420 to various degrees across the beam field. Beam-modulating filter 415 may be any device capable of selectively altering an amount attenuation of initial beam 410 to various degrees across the beam field, thereby creating spatially modulated beam 110. Similar to spatially modulated beam 110 in FIG. 1, beam-modulating filter 415 may attenuate initial beam 410 as to create a desired beam 110 intensity field, as described above.

In an example, beam-modulating filter 415's ability to selectively alter beam attenuations across the beam field may be compared to a liquid crystal display ("LCD") device. For example, an LCD device may control the passage of light through pixels by applying an electric current to a matrix of liquid crystals. By application of the proper current, individual pixels of the LCD may change to allow variable amounts of light through an LCD. Similarly, beam-modulating filter 415 may employ a matrix of pixels that, based on a modulator configuration signal 420 may change to allow various amounts of x-ray beam 410 to pass, for example.

The functions of the remaining components of system 400 are similar to those of system 100 depicted in FIG. 1 and are described above. The functionality, applications, and benefits of system 400 are similar to the functionality of system 100 in FIG. 1. For example, sources 105 and 405, object 120, detector 140, beam processor 160, image processor 170, and display device 195 may behave similarly in both FIGS. 1 and 4.

Figure 5:
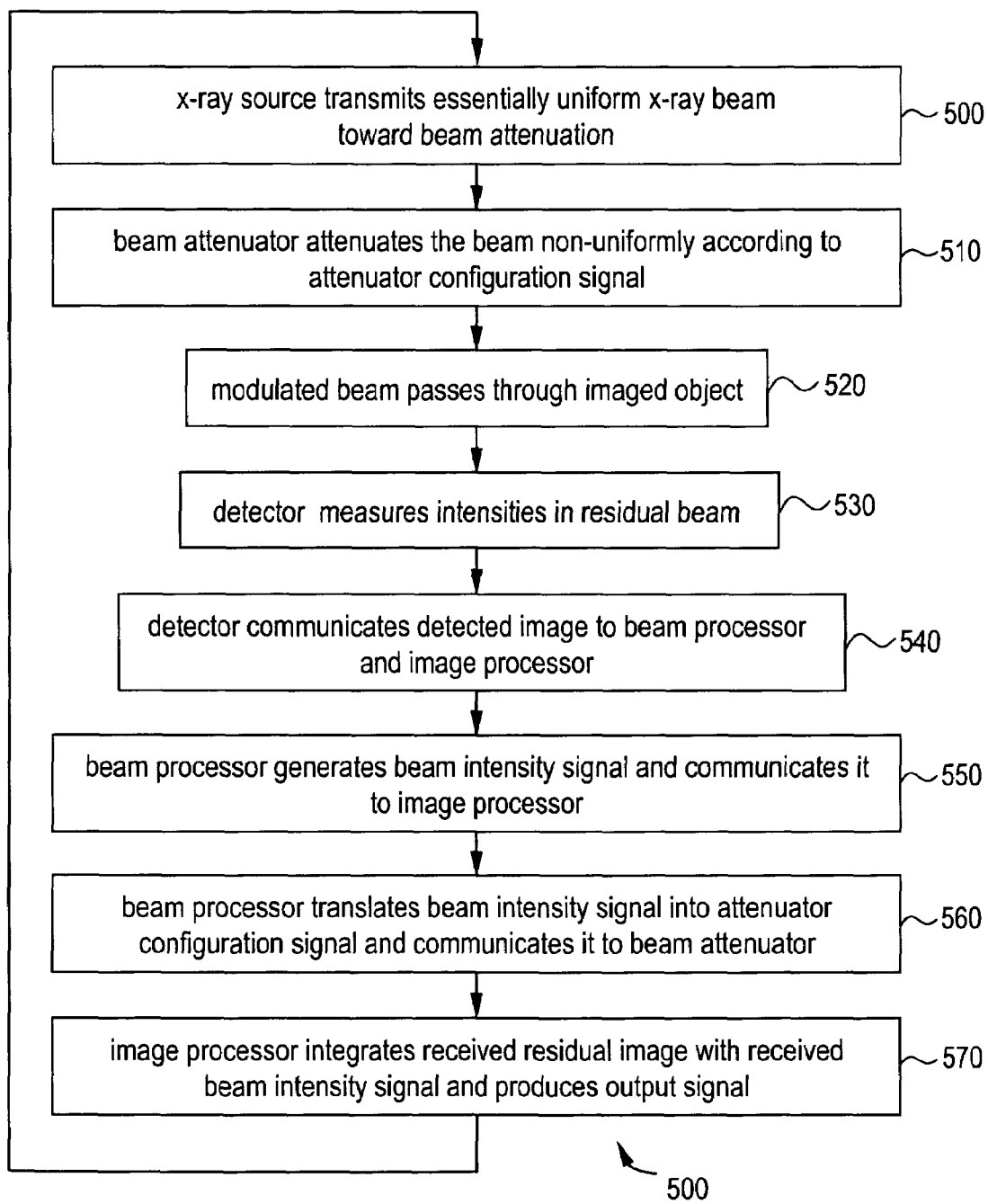
FIG. 5 illustrates a flowchart according to a method of generating an output image signal based on the above described feedback loop using a beam-modulating filter in accordance with an embodiment of the present invention.

FIG. 5 illustrates a flowchart according to a method 500 of generating an output image signal 190 based on the above described feedback loop using a beam-modulating filter in accordance with an embodiment of the present invention. First, at step 505, an x-ray source 405 transmits an x-ray beam 410 towards a filter or beam attenuator 415, as described above. Next, at step 510, a beam attenuator (or filter) 415 attenuates the beam 410, as described above. For example, attenuator 415 may attenuate the beam 410 non-uniformly according to a modulator configuration signal 420. Once beam 410 has exited the attenuator 415, beam 410 becomes modulated beam 110, as described above. Modulated beam 110 then passes through an imaged object 120 and becomes a residual beam 130, as shown in step 520. The residual beam 130 then strikes a detector 140. At step 530 the detector 140 measures the x-ray intensities of the residual beam 130 in order to create a residual image 150. Next, at step 540, the detector 140 communicates the residual image 150 to a beam processor 160 and an image processor 170, as described above. At step 550, the beam processor 160 generates a beam intensity signal 180 and communicates the intensity signal 180 to the image processor 170. Next, at step 560, the beam processor 160 translates the beam intensity signal 180 into a configuration signal 420, as described above, and communicates the signal 420 to the beam attenuator 415. Next, at step 570, the image processor 170 integrates the residual image 150 with the beam intensity signal 180 in order to produce an output image signal 190, as described above. This image signal 190 may then be communicated to a display device 195 for display. Next, method 500 may proceed to step 505. In this way, method 500 may proceed in a feedback loop manner.

The basis for a practical embodiment of a beam-modulating filter in accordance with this invention is referred to as "x-ray dodging". The term originates from the dodging and burning techniques in darkroom light photography. To control the exposure to a portion of a photograph, photographers may introduce an opaque mask into the light beam for a calculated portion of the exposure time. To feather sharp mask edges in the photograph, photographers may wave the mask horizontally or vertically. The photographic paper integrates the exposure over time, so that the variations of total exposure to the photographic paper may be controlled across the image by the duration of time for which the region remains blocked by the mask.

Beam-modulating filters previously disclosed (for example, as described above) modulate the beam by varying the thicknesses of the semi-transparent substances placed in the x-ray beam. In contrast, x-ray dodging uses radiographically opaque elements to block the beam completely but only for a controlled portion of a frame integration period. This strategy endows the beam modulator with flexibility, a high number of gradation levels, high spatial resolution, and a high dynamic range. In addition, unlike the previous attempted solutions (as described above), beam modulation using x-ray dodging is not as sensitive to x-ray photon energies as long as the x-ray blocking elements remain radiographically opaque. In the range of x-ray techniques used for interventional medical fluoroscopy and diagnostic radiography, elements made of 0.8-1.5 mm of tungsten may be sufficient to effectively block the x-ray beam.

To control the exposure times, the x-ray-blocking elements may be moved, rotated, and/or oscillated at high speeds or frequencies with high precision. To help reduce the complexity of the motion, the intensity of the uniform beam may be varied synchronized with the motion of the x-ray blocking elements. In practice, it may be easier to make these motions and beam intensity variations periodic in time. Therefore, the x-ray dodging technique may be defined as the use of controlled arrangements of x-ray blocking elements in the x-ray beam undergoing a high-frequency periodic motion synchronized with periodic temporal x-ray beam modulations and detector frame integration periods to produce desired spatial modulation of the x-ray beam.

Figure 8:
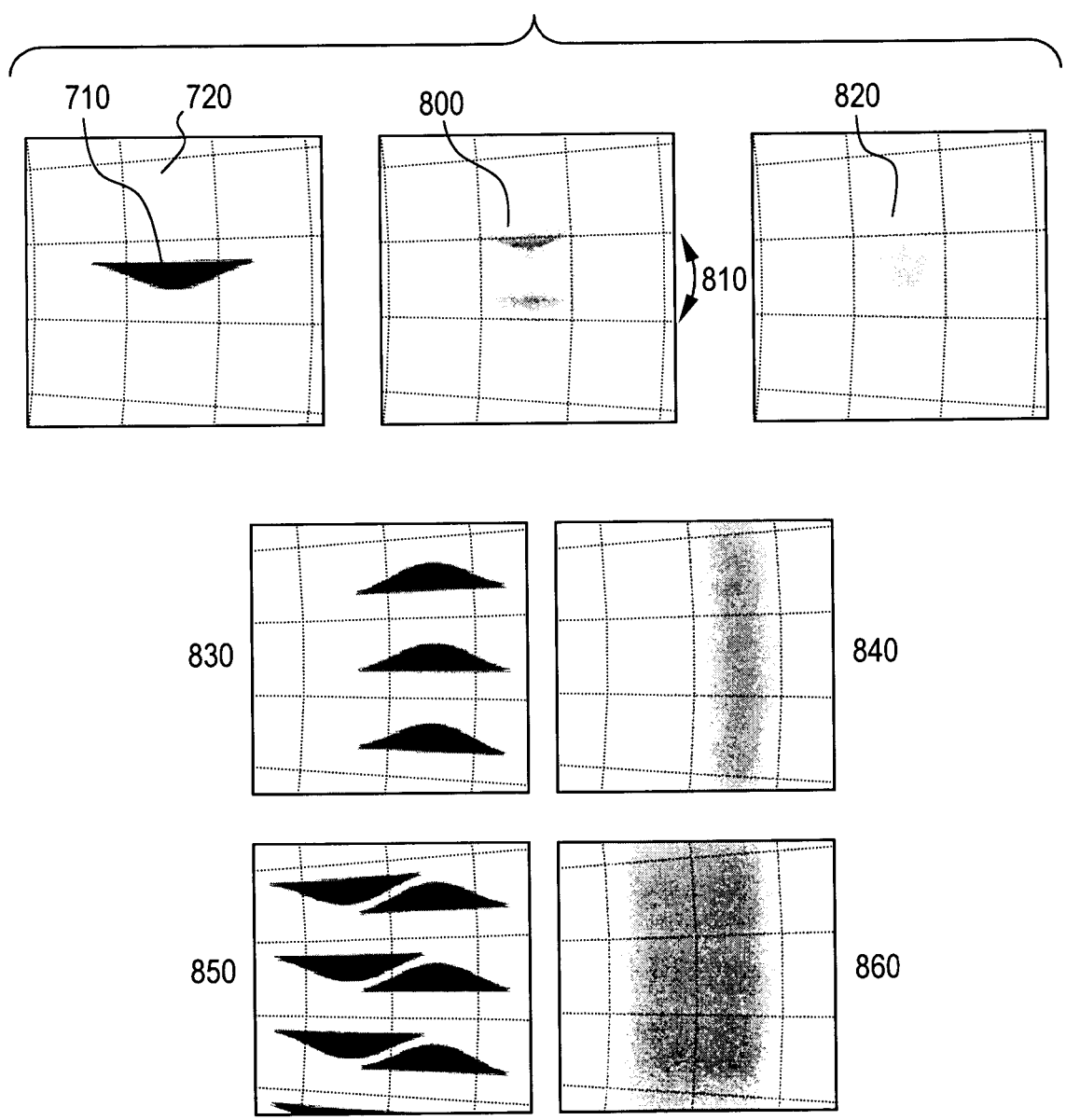
FIG. 8 illustrates the effect of x-ray dodging according to an embodiment of the present invention.

FIG. 8 illustrates the effect of x-ray dodging according to an embodiment of the present invention. In this embodiment exposed area 615 is divided into image cells 720. A radiographically opaque element 710 may be introduced into any image cell. When the element 710 undergoes an oscillatory motion 810 at a high frequency in a plane perpendicular to the x-ray beam with the amplitude of about one cell width, a semitransparent blurred attenuation pattern 800 may be produced. Here the oscillation 810 is assumed to be harmonic or sinusoidal. The oscillatory motion 810 may not completely remove sharp features from the attenuation pattern 800. These sharp features may introduce artifacts in an output image 190. To remove these sharp features, the system may vary the intensity of the initial uniform beam 410 synchronized with the phase of the oscillatory motion 810.

For example, let $\phi_k(\theta,\rho) \in [0,1]$ be the attenuation function of the $k^{th}$ basis disc defined in polar coordinates $\theta,\rho$ such that the center of disc rotation 630 is at $\rho=0$. The system will then shift the phases 640 of each disc k by appropriate angular offsets $\psi_k$ to produce a desired combined attenuation function of the entire stack $$\Phi(\theta, \rho) = \prod_k \phi_k(\theta + \psi_k, \rho).$$

Figure 6:
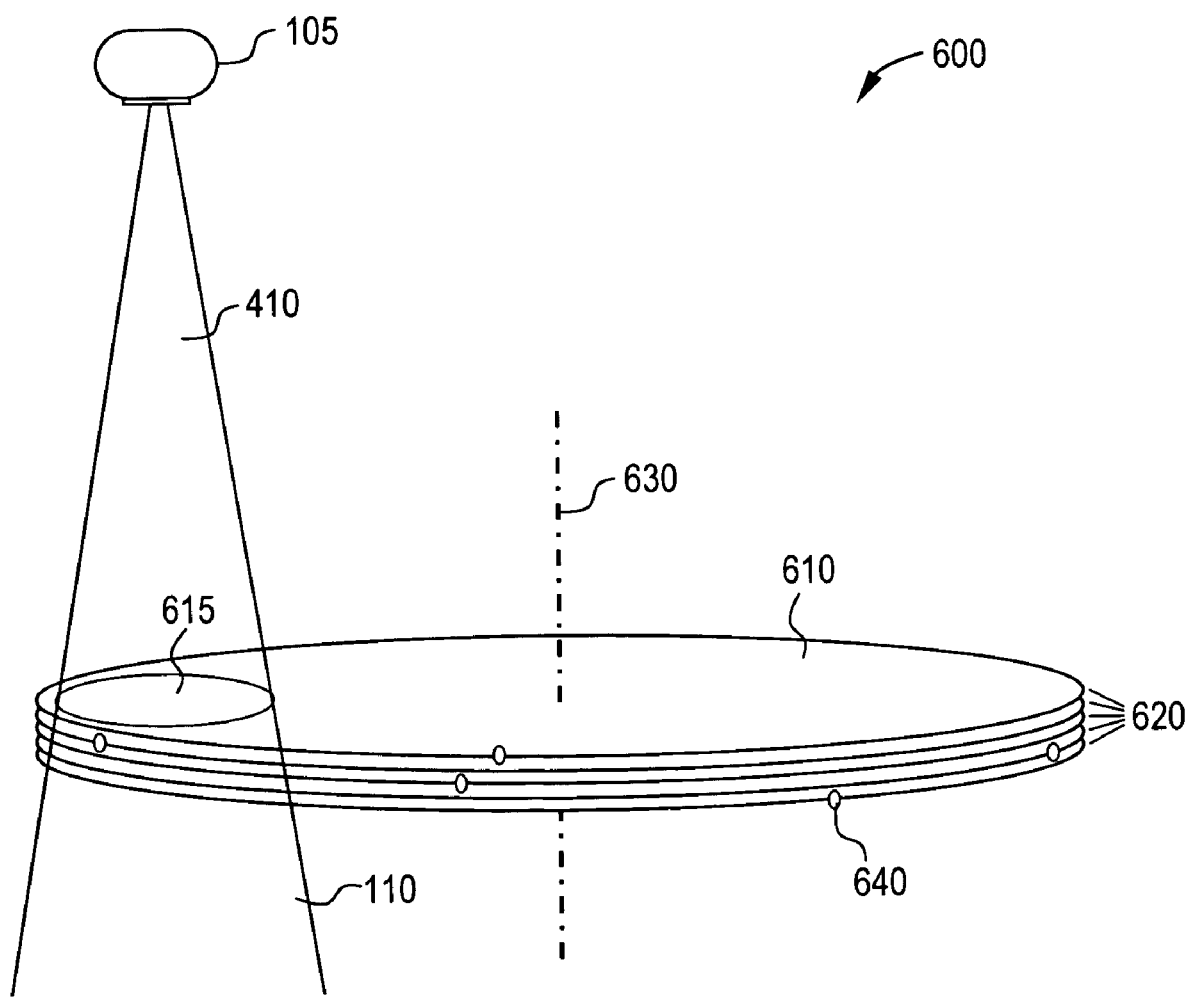
FIGS. 6 and 7 illustrate an embodiment of the beam-modulating filter in accordance with an embodiment of the present invention.

Indicators 640 representing one or more phase shifts are included in FIG. 6 for demonstration purposes only. The entire disc stack 610 is caused to undergo rotational oscillation so that its angular offset $\epsilon$ varies as $$\varepsilon = \lambda \cos\left(\frac{2\pi t}{T}\right),$$

where t is time, T is the oscillation period, and $\lambda$ is the angular oscillation amplitude $$\lambda = \frac{\pi}{64}$$

Now, a portion of the disc stack is exposed to a uniform beam with time-varying intensity $I_0(t)$. Then at any point in time t, the intensity of the modulated beam will be $I(\theta,\rho,t) = I_0(t) \cdot \Phi(\theta+\epsilon(t),\rho)$. The mean intensity during each half period will be:

$$I(\theta, \rho) = \frac{2}{T} \int_0^{\frac{T}{2}} I_0(t) \cdot \Phi(\theta + \varepsilon(t), \rho) \cdot dt.$$

Substituting the integration variable to $\epsilon$, this expression becomes $$I(\theta, \rho) = \frac{2}{T} \int_{-\lambda}^{\lambda} I_0\left(\frac{T}{2\pi}\cos^{-1}\frac{\varepsilon}{\lambda}\right) \cdot \Phi(\theta - \varepsilon, \rho) \cdot \frac{T}{2\pi\lambda} \cdot \frac{1}{\sqrt{1 - \left(\frac{\varepsilon}{\lambda}\right)^2}} dt.$$

This may be written as a convolution integral $I(\theta,\rho) = h(\theta) * \Phi(\theta,\rho)$, where $$h(\theta) = I_0\left(\frac{T}{2\pi}\cos^{-1}\frac{\theta}{\lambda}\right) \cdot \frac{T}{2\pi\lambda} \cdot \frac{1}{\sqrt{1 - \left(\frac{\theta}{\lambda}\right)^2}}.$$

Now it may be shown that, by modifying the time intensity waveform $I_0(t)$ of the uniform x-ray beam 410, one can effectively convolve the attenuation pattern $\Phi(\theta,\rho)$ with an arbitrary function $g(\theta)$ along the $\theta$ axis. For example, one may choose $g(\theta)$ to be a smoothing band-limiting kernel such as a Gaussian or Hanning kernels. Then $h(\theta)=g(\theta)$ and beam intensity waveform may be computed as $$I_0(t) = g\left(\lambda \cos\frac{2\pi t}{T}\right) \cdot \frac{2\pi\lambda}{T} \cdot \sin\frac{2\pi t}{T} \text{ for } t = \left[0, \frac{T}{2}\right]$$

(a single pulse). Pulses may be spread out or follow each other in sequence, as required by the imaging application.

Figure 9:
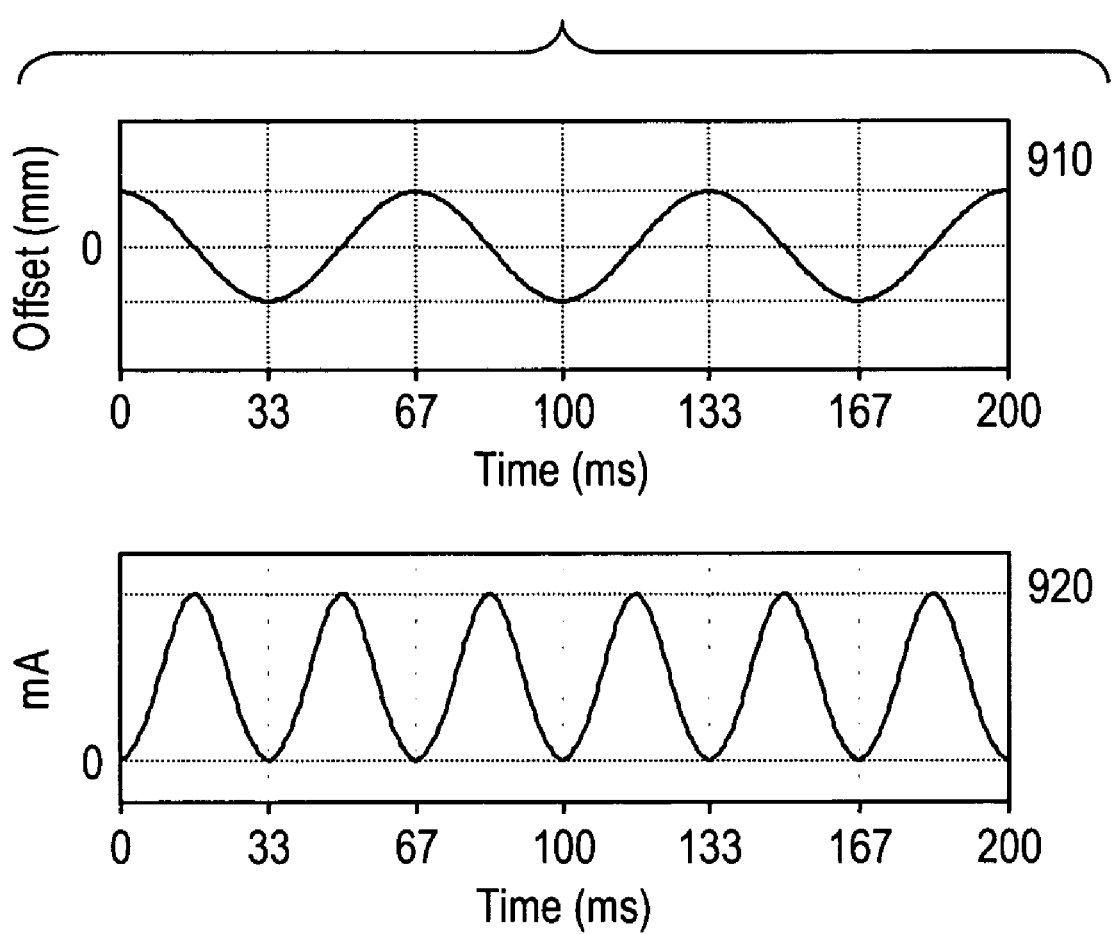
FIG. 9 illustrates an x-ray tube current waveform such as 920 may be used to smoothen motion blur produced by the harmonic oscillation such as 910 in accordance with an embodiment of the present invention.

FIG. 9 illustrates an example of an oscillation offset function 910 that may correspond to the harmonic oscillation function $\epsilon(t)$ described above and the x-ray tube current waveform 920 (mA) that produces proportional uniform beam 410 intensity $I_0(t)$ as described above. The x-ray tube waveform 920 causes the smoothing kernel $h(\theta)$ to become a Gaussian kernel, resulting in a smoothing effect such as illustrated in FIG. 8.

Notice that the motion blurring in FIG. 8 smoothens the attenuation pattern along the direction of oscillation 810 only. The smoothness along the radial axis is achieved due to smooth variations of the widths of the x-ray blocking elements 710. When a column of x-ray blocking elements 830 is smoothened by oscillations 810 synchronized with beam intensity modulation 920 of FIG. 9, the resulting beam modulation pattern 840 may be made completely uniform along the direction of oscillation 810 due at least in part to the band-limited convolution kernel $h(x)$. Rows of beam blocking elements 850 may result in uniform attenuation orthogonal to oscillation 810 due at least in part to the band-limited width variations of the x-ray blocking elements 710. In this way, the x-ray block elements 710 combined with periodic motion 810 and temporal beam intensity modulation may be used to produce smoothly varying attenuation patterns. These patterns may be critical to avoid image artifacts or the necessity for perfect beam alignment.

Figure 10:
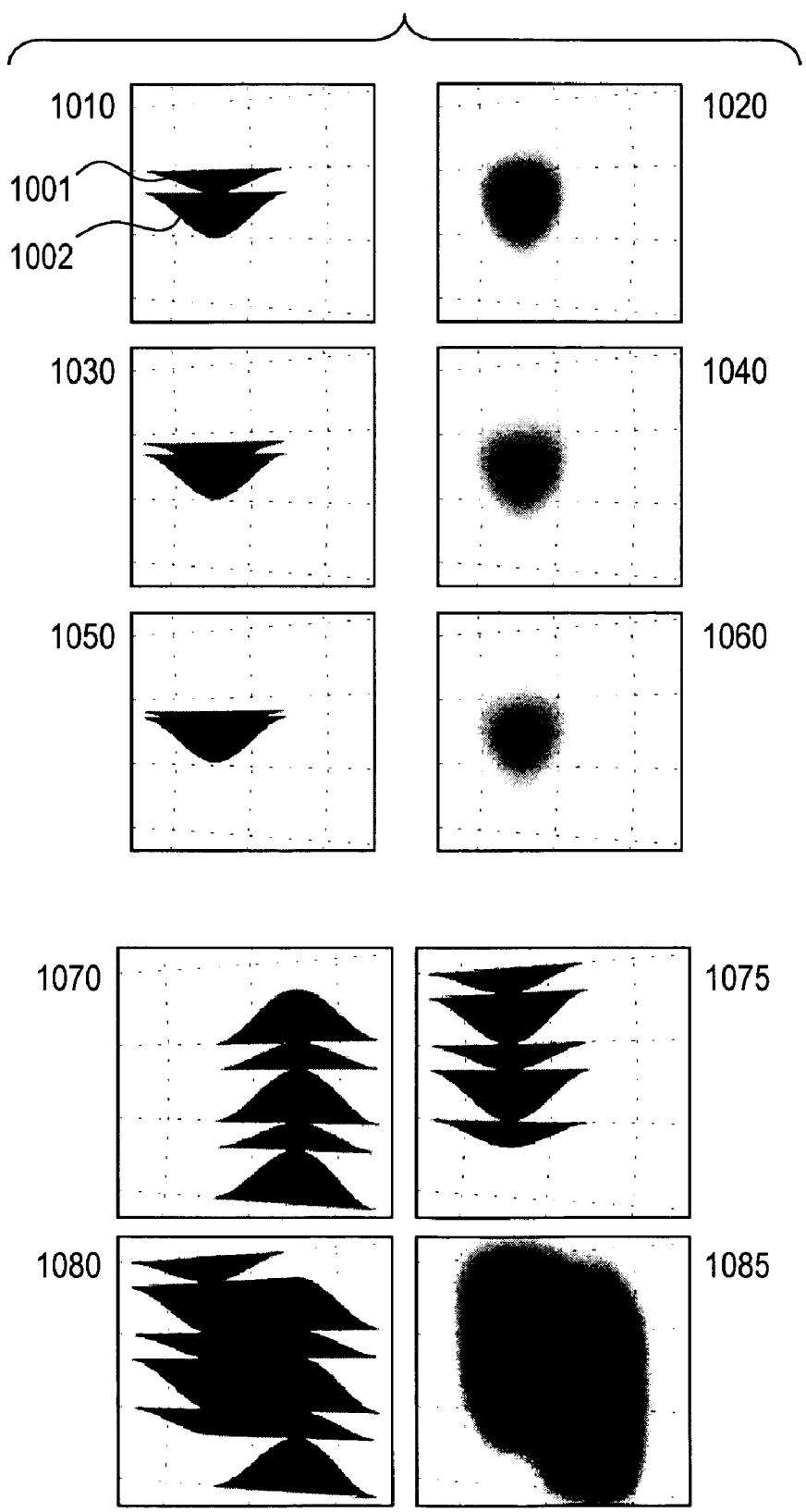
FIG. 10 illustrates a more flexible way to adjust the local attenuation level with the use of inter-element occlusions according to an embodiment of the present invention.

Motion blur and temporal beam modulation remove sharp features from the attenuation pattern. The area blocked by a beam-blocking element 710 will contribute to the attenuation produced in the image cell in which it is placed. The system may regulate the local attenuation by selecting from a set of possible beam-blocking elements of various widths. FIG. 10 illustrates a more flexible way to adjust the local attenuation level with the use of inter-element occlusions according to an embodiment of the present invention. Two beam-blocking elements 1001 and 1002 may be placed in the beam. Elements 1001, 1002 may differ in size and/or shape. If these elements 1001, 1002 are positioned in different planes, they may occlude one another. As a result, the total beam-blocking areas may be varied gradually, with the number of attenuation levels limited only by the mechanical precision.

For example, when the two elements 1001, 1002 are not occluding each other, as in element arrangement 1010, the resulting attenuation cell 1020 may be darker than when the elements 1001, 1002 occlude each other to various degrees, as in element arrangements 1030 and 1050 and corresponding attenuation cells 1040 and 1060). In addition, other ways of changing the projected area of a beam-blocking element may be used such as rotation of the element or moving the element closer to or away from the focal spot.

The design of x-ray-blocking elements may also take into consideration how adjacent cells interact. For example, it may be desirable to have the capability to block a portion of the x-ray beam completely. In order to do so, rows and/or columns of elements may mesh tightly so that the x-ray beam is blocked completely. Beam-blocking elements are designed to interlock with elements from adjacent rows as to be configurable to block an entire area without gaps. For example, two adjacent columns of cells 1070 and 1075 of elements set for maximum attenuation, when combined, may lock tightly as in arrangement 1080. After they are blurred by motion, the smoothened attenuation pattern 1085 contains areas where the beam is completely blocked.

Inter-element occlusions are just one of several possible approaches of blocking varying portions of the x-ray beam with one or several beam-blocking elements. For example, rotating or rolling the elements or moving them toward or away from the x-ray source may be employed. Neither do inter-element occlusions need to be limited to two elements. Multiple elements occluding one another in various arrangements may provide even greater flexibility in creating desired attenuation patterns.

Figure 7:
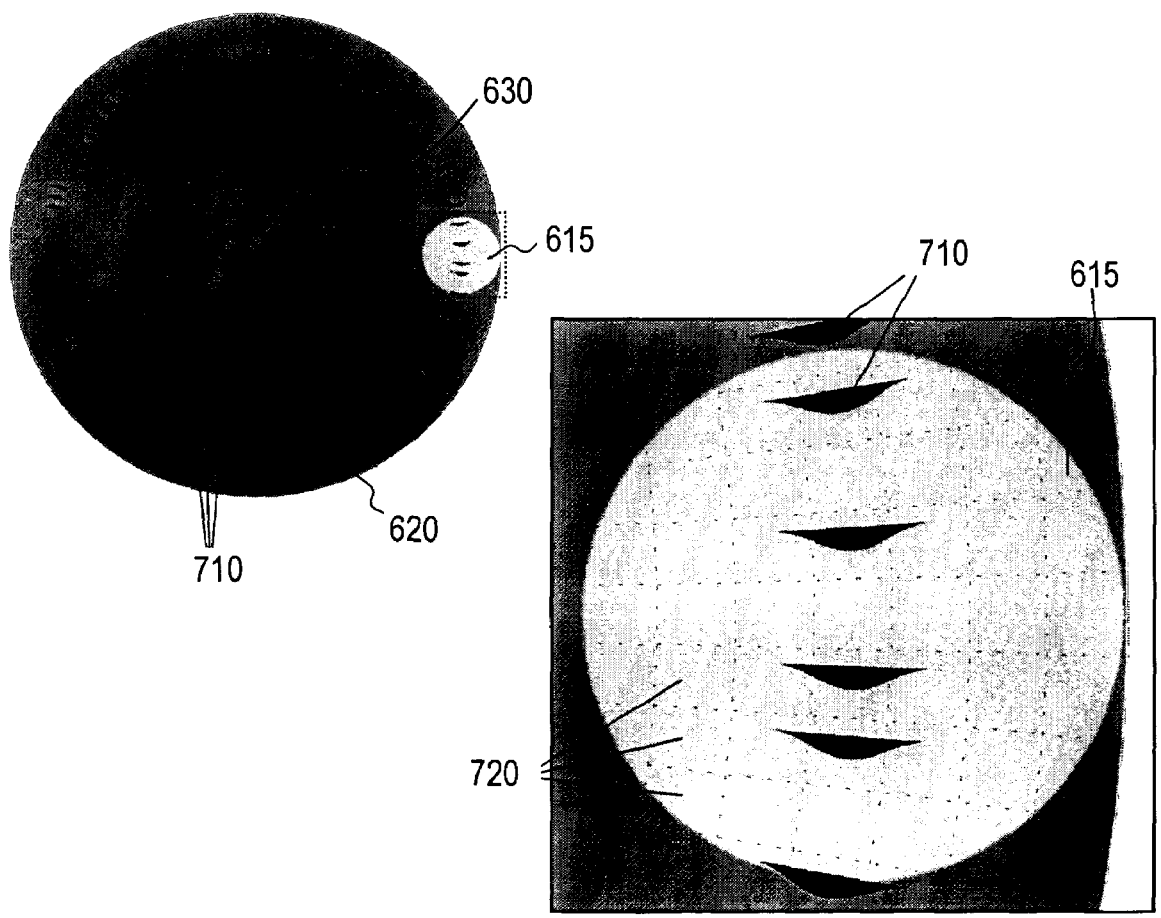

FIG. 6 and FIG. 7 each illustrate an embodiment of the beam-modulating filter 415 in accordance with an embodiment of the present invention. The x-ray source 105 produces an essentially uniform x-ray beam 410, as described above. The uniform x-ray beam 410 traverses a stack of disc-shaped basis filters 620. The basis filters 620 are made of a radiographically translucent material and contain arrangements of x-ray-blocking elements 710.

The relative angular offsets 640 of the basis discs place different portions of each disc in the exposed area 615. For example, angular offset 640 of a given disc may be determined by an angular offset 640 of a particular x-ray blocking element 710 or other known position marker indicated by reference 635. The discs' angular offsets may be controlled independently. By varying the number of discs 620, the various arrangements of elements 710, and the various angular displacements of the various discs 620, a large number of possible arrangements of x-ray blocking elements in the exposed area 615 are possible.

The entire disc stack may be caused to undergo a high-frequency rotational oscillation around the axis 630 synchronized with the periodic temporal modulation of the uniform beam 410.

The rotational offsets of the basis discs may be controlled by the modulator configuration signal 420 originating from the beam processor 160, as described above. The motors and mechanics driving these offsets are not shown in FIG. 6, but may be embodied, for example, in a stepper motor configuration known to those of ordinary skill in the art.

In an example of an embodiment of the present invention, the circular exposed area 615 of a basis filter 620 may be divided into columns and rows of cells 720, as shown in FIG. 7. For example, in FIG. 7, the exposed circular area 615 is divided into five 7-cell central columns and two 3-cell boundary columns. The beam attenuation level of each of the 41 cells can be controlled independently with smooth transitions between them.

Two basis discs are assigned to each of the five central columns of image cells (ten basis discs total). Each disc 620 may be rotated to such a position that each cell 720 in the exposed column will either include an x-ray-blocking element or not contain one. For a seven-cell column, $2^7=128$ such septuplets are possible. If 1 represents the presence of an x-ray-blocking element and 0 represents the absence of an x-ray-blocking element, then arranging the elements circularly around a basis disc according to the 128-element pattern 0 0 0 0 1 1 1 0 0 0 0 1 1 0 1 1 1 1 1 0 1 1 0 0 1 0 0 1 1 1 1 1 1 1 1 0 0 1 1 0 0 0 1 0 1 0 1 0 1 1 1 1 0 0 0 1 1 0 0 1 1 1 0 1 0 1 1 0 1 1 0 1 0 1 0 0 1 1 0 1 0 0 0 1 0 0 1 0 0 0 1 1 1 1 0 1 0 0 1 0 1 1 1 0 1 1 1 0 0 1 0 1 0 0 0 0 1 0 1 1 0 0 0 0 0 1 0 0 can allow rotating the disc 620 to a position producing any possible such septuplet. Since two discs may be assigned to each column, for each of the 35 central cells, four possible configurations are possible: (1) no x-ray block elements present, (2) one x-ray blocking element from first basis disc present, (3) one x-ray-blocking element from second basis disc present, and (4) two x-ray-blocking elements present, one from the first and one from the second basis disc. For example, if the resulting cell attenuation from an element from the first disc is 0.33 and from the second disc—0.67, then when both elements are present in the cell, the attenuation may be varied in continuous gradation from 0.67 to 1.0 by adjusting the degree of the inter-element occlusions.

Many other pattern designs are possible, not necessarily based on cell matrices. For example, in a circular exposed area such as 615 in FIG. 7, the vertical boundary columns contain only three cells. Instead of using two discs with a binary pattern of beam-blocking elements such 715 as described above to provide four independent attenuation levels, a quinternary attenuation pattern may be used to provide any of five attenuation patterns in each cell, independently. An example of such 125-cell circular pattern is 0 0 1 1 1 2 2 2 3 3 3 4 4 4 1 1 3 3 0 0 2 2 4 4 2 2 0 0 3 3 1 1 4 4 3 3 2 2 1 1 0 0 4 4 0 1 2 3 4 0 2 3 0 1 3 4 1 2 4 0 3 4 3 4 2 3 2 3 1 2 1 2 0 2 4 2 4 1 3 1 3 0 3 0 2 0 1 0 1 4 1 4 2 0 3 1 4 0 4 1 0 2 1 3 2 4 3 0 4 2 1 4 3 1 0 3 2 0 4 3 2 1 0 4 0. In this pattern any contiguous triplet of digits 0 through 4 may be found. If five types of beam blocking elements corresponding to these digits are arranged in a circle on a disc, then any combination of such elements may be selected into the three exposed cells.

While particular elements, embodiments and applications of the present invention have been shown and described, it is understood that the invention is not limited thereto since modifications may be made by those skilled in the art, particularly in light of the foregoing teaching. It is therefore contemplated by the appended claims to cover such modifications and incorporate those features that come within the spirit and scope of the invention.

What is claimed is:

1. An x-ray imaging system using spatial modulation of an x-ray beam, said system including:
    an x-ray source transmitting said beam towards an object to be imaged, said x-ray source generating said beam so that said beam includes a plurality of x-ray intensities varying spatially and temporally and based on at least a beam intensity signal;
    an x-ray detector receiving said beam after an interaction between said beam and said object, said detector measuring a plurality of residual intensities of said beam and producing a residual image signal based on at least said residual intensities;
    a beam processor creating said beam intensity signal based on at least one of a previous beam intensity signal, said residual intensities, a region of interest in said object, and anticipated object motion; and
    an image processor producing an output image signal, said output image signal based on one or more of said residual image signal and said beam intensity signal.

2. The system of claim 1, wherein said plurality of x-ray intensities is dynamically altered by said x-ray source.

3. The system of claim 1, wherein said plurality of x-ray intensities is altered by said x-ray source to match one or more of a distribution of anticipated radiographic thicknesses in said imaged object, a distribution of said regions of interest in said imaged object, and a distribution of regions of motion in said imaged object.

4. The system of claim 1, wherein said beam intensity signal is based on at least said residual image signal.

5. The system of claim 1, further including a filter, said filter filtering said beam transmitted by said x-ray source by altering amounts of attenuation of said beam.

6. The system of claim 5, wherein said filter creates said spatially modulated beam using x-ray dodging.

7. The system of claim 5, wherein said filter creates said spatially modulated beam by moving an arrangement of radiographically opaque elements during an image integration period so that such motion causes various regions in said beam to be blocked for various portions of said image integration period in said x-ray detector.

8. The system of claim 7, wherein at least one of said radiographically opaque elements changes a spatial orientation or occludes another element to alter said beam transmitted by said x-ray source.

9. The system of claim 7, wherein said arrangement of radiographically opaque elements are produced by configurable juxtapositions of a plurality of basis filters, each of said basis filters including a combination of said radiographically opaque elements.

10. The system of claim 5, wherein said beam processor converts said beam intensity signal into a modulator configuration signal and communicates said modulator configuration signal to said filter, and said filter alters said amounts of attenuation based on at least said modulator configuration signal.

11. The system of claim 10, wherein said modulator configuration signal causes a position of one or more of said basis filters to change.

12. The system of claim 1, wherein said x-ray source transmit so that said beam varies temporally during an image integration period.

13. A method for x-ray imaging with spatial modulation of an x-ray beam, said method including:
transmitting said beam towards an object to be imaged, an x-ray intensity field of said beam varying across said beam, said intensity field based on at least a beam intensity signal;
receiving said beam at an x-ray detector;
measuring a plurality of intensities of said beam at said detector;
creating a residual image signal based on at least said intensities measured at said detector; and
producing an output image signal, said output image signal based on one or more of said residual image signal and said beam intensity signal,
wherein said beam intensity signal is based on one or more of a predicted information density and said intensities measured at said detector.

14. The method of claim 13, further including dynamically altering said beam intensity field.

15. The method of claim 13, wherein said beam intensity field includes one or more of a distribution of radiographic thicknesses in imaged object, a distribution of regions of interest, and a distribution of regions of anticipated object motion.

16. The method of claim 13, wherein said beam intensity signal is based on at least said residual image.

17. The method of claim 13, wherein said transmitting step includes transmitting an essentially uniform x-ray beam and further including creating a spatially modulated x-ray beam by filtering said essentially uniform beam, said creating step including altering an amount of attenuation of said essentially uniform beam to various degrees across said essentially uniform beam.

18. The method of claim 17, further including employing x-ray dodging to create said beam intensity field.

19. The method of claim 18, wherein said employing x-ray dodging step includes moving one or more configurable arrangements of radiographically opaque elements during an image integration period of said detector so that various portions of said essentially uniform beam remain blocked for various portions of said image integration period.

20. The method of claim 17, further including:
converting a beam intensity signal into a modulator configuration signal, wherein said field is based on at least said beam intensity signal; and
communicating said modulator configuration signal to a filter, wherein said creating step includes employing said filter in order to alter said amount of attenuation based on at least said modulator configuration signal.

21. The method of claim 13, further including varying said x-ray intensity field temporally during an image integration period.

22. A system for creating an x-ray image using spatial modulation of an x-ray beam, said system including:
an x-ray source producing said beam toward an object to be image, wherein said object includes at least one predicted information density, said predicted information density including at least one of a radiographic thickness, a region of interest, and a region of object motion, said beam including a field of continually varying x-ray intensities;
an object to be imaged including at least one predicted information densities, said predicted information density including at least one of a radiographic thickness, a region of interest, and a region of object motion;
a detector creating a residual image based on at least x-ray intensities of said beam received at said detector and attenuated by one or more of said object and said predicted information density; and
a beam processing unit examining said residual image in order to determine at least one modification to said field of continually varying x-ray intensities transmitted in at least one subsequent beam transmitted by said source.

23. The system of claim 22, wherein said beam processing unit communicates said modification to said field of continually varying x-ray intensities to one or more of said source and a filter disposed between said source and said object.

24. The system of claim 22, wherein said beam processing unit continually modifies said field of continually varying x-ray intensities in subsequent beams transmitted by said source.

25. The system of claim 22, wherein said beam processing unit modifies said field of continually varying x-ray intensities in at least one subsequent beam transmitted by said source based on at least a change in said predicted information density.

26. The system of claim 22, further including an image processing unit combining a representation of said x-ray intensity field and said residual image to create an output image.

27. The system of claim 26, wherein said beam processing unit and said image processing unit are included in an external beam modification device to augment a conventional system with dynamic beam modulating capabilities.

28. An imaging system, comprising:
a source transmitting a beam of energy toward an object to be imaged;
a detector receiving a residual beam of the beam of energy after it passes through the object wherein said detector measures beam intensities in the residual beam; and
a beam processor receiving data related to the beam intensities and communicating a beam intensity signal to said source, wherein said source alters and spatially modulates the beam of energy according to the beam intensity signal.

29. The imaging system of claim 28, further comprising:
an image processor that receives residual image data based on the residual beam and produces a displayed image signal; and
a display that receives the displayed image signal.

30. The imaging system of claim 28, wherein the beam of energy is an x-ray beam.

31. The imaging system of claim 28, wherein the spatially modulated beam is constructed to match a distribution of radiographic thicknesses of the object.

32. The imaging system of claim 28, wherein the spatially modulated beam is constructed to match a distribution of a region of interest of the object.

33. The imaging system of claim 28, wherein the spatially modulated beam is constructed to match a distribution of regions of sustained motion in the object.

34. The imaging system of claim 28, wherein said beam processor completes a feedback loop that one of periodically and continuously updates a beam intensity field.

35. The imaging system of claim 28, further comprising a beam-modulating filter positioned between said source and the object.

36. The imaging system comprising:
a source transmitting a beam of energy toward an object to be imaged;
a detector receiving a residual beam of the beam of energy after it passes through the object wherein said detector measures beam intensities in the residual beam; and
a beam processor receiving data related to the beam intensities and communicating a beam intensity signal to said source,
wherein said source alters and spatially modulates the beam of energy according to the beam intensity signal, and
wherein said source alters the beam of energy by moving a narrow beam back and forth in a raster pattern over particular areas of the object while varying the beam's intensity temporally.

37. An imaging method, comprising:
transmitting a beam of energy toward an object to be imaged with a source;
measuring beam intensities in a residual beam;
receiving data related to the beam intensities;
communicating a beam intensity signal to the source, and spatially modulating the beam of energy based on said communicating.

38. The method of claim 37, wherein the beam of energy is an x-ray beam.

39. The method of claim 37, wherein said spatially modulating comprises matching the beam of energy to a distribution of radiographic thicknesses of the object.

40. The method of claim 37, wherein said spatially modulating comprises matching the beam of energy to a region of interest of the object.

41. The method of claim 37, wherein said spatially modulating comprises matching a distribution of regions of sustained motion in the object.

42. The method of claim 37, further comprising one of periodically and continuously updating a beam intensity field.

43. A system for creating an x-ray image using spatial modulation of an x-ray beam, said system including:
a beam processing unit examining a residual image in order to determine at least one modification to a field of varying x-ray intensities transmitted in at least one subsequent x-ray beam transmitted by an x-ray source, the x-ray source generating said beam so that said beam includes a plurality of x-ray intensities varying spatially and temporally,
wherein said x-ray source produces said subsequent x-ray beam towards an object to be imaged, said object including at least one predicted information density that includes at least one of a radiographic thickness, a region of interest, and a region of object motion,
wherein said residual image is created by an x-ray detector and is based on at least x-ray intensities of an x-ray beam received at said detector previous to said subsequent x-ray beam and attenuated by one or more of said object and said predicted information density.

44. The system of claim 43, wherein said beam processing unit modifies said field of x-ray intensities in at least one subsequent beam transmitted by said source.

45. The system of claim 43, wherein said beam processing unit communicates said modification to one or more of said source and a filter disposed between said source and said object.

46. The system of claim 43, wherein said beam processing unit modifies said field of x-ray intensities in at least one subsequent beam transmitted by said source based on at least a change in said predicted information density.

47. The system of claim 46, wherein said beam processing unit and said image processing unit are included in an external beam modification device of an x-ray imaging system.

48. The system of claim 43, further including an image processing unit combining a representation of said x-ray intensity field and said residual image to create an output image.

* * * * *

UNITED STATES PATENT AND TRADEMARK OFFICE
CERTIFICATE OF CORRECTION

PATENT NO. : 7,272,208 B2
APPLICATION NO. : 10/945649
DATED : September 18, 2007
INVENTOR(S) : Yatsenko et al.

It is certified that error appears in the above-identified patent and that said Letters Patent is hereby corrected as shown below:

At column 13, line 17, after the word "amplitude", insert --(e.g.--.

At column 13, line 21, after " $\lambda = \dfrac{\pi}{64}$ " insert --).--.

At column 13, line 36, delete "$\epsilon$" and substitute therefor --ε--.

At column 17, line 26, delete "transmit" and substitute therefor --transmits--.

Signed and Sealed this
Eighth Day of February, 2011

David J. Kappos
*Director of the United States Patent and Trademark Office*